United States Patent
Shirahama

(10) Patent No.: US 12,343,250 B2
(45) Date of Patent: Jul. 1, 2025

(54) MEMBRANE BODY FOR TUBULAR TREATMENT DEVICE AND TUBULAR TREATMENT DEVICE

(71) Applicant: SB-KAWASUMI LABORATORIES, INC., Kawasaki (JP)

(72) Inventor: Noriaki Shirahama, Kawasaki (JP)

(73) Assignee: SB-KAWASUMI LABORATORIES, INC., Kawasaki (JP)

( * ) Notice: Subject to any disclaimer, the term of this patent is extended or adjusted under 35 U.S.C. 154(b) by 651 days.

(21) Appl. No.: 17/640,214

(22) PCT Filed: Aug. 20, 2020

(86) PCT No.: PCT/JP2020/031434
§ 371 (c)(1),
(2) Date: Mar. 3, 2022

(87) PCT Pub. No.: WO2021/044858
PCT Pub. Date: Mar. 11, 2021

(65) Prior Publication Data
US 2022/0331088 A1   Oct. 20, 2022

(30) Foreign Application Priority Data
Sep. 4, 2019 (JP) ................... 2019-160915

(51) Int. Cl.
*A61F 2/07* (2013.01)
(52) U.S. Cl.
CPC .......... *A61F 2/07* (2013.01); *A61F 2002/075* (2013.01); *A61F 2210/0076* (2013.01); *A61F 2220/0075* (2013.01)

(58) Field of Classification Search
CPC ................... A61F 2002/075; A61F 2210/0076
See application file for complete search history.

(56) References Cited

U.S. PATENT DOCUMENTS

| | | | |
|---|---|---|---|
| 6,709,455 B1 | 3/2004 | Chouinard | |
| 8,337,546 B2 | 12/2012 | Bruszewski | |
| 9,839,542 B2 | 12/2017 | Bruszewski et al. | |
| 2005/0149165 A1* | 7/2005 | Thistle | A61F 2/07 623/1.13 |
| 2020/0345474 A1 | 11/2020 | Yokota | |

FOREIGN PATENT DOCUMENTS

| | | |
|---|---|---|
| EP | 2 103 278 | 9/2009 |
| JP | S55-54950 | 4/1980 |
| JP | H 06-77600 | 10/1994 |
| WO | WO 00/09041 | 2/2000 |
| WO | WO 02/49536 | 6/2002 |

OTHER PUBLICATIONS

Office Action issued Jul. 9, 2024 in corresponding Japanese patent application No. 2021-543690.
Extended European Search Report issued in corresponding European Application No. 20861851.2, dated Jun. 30, 2023.

* cited by examiner

*Primary Examiner* — Javier G Blanco
(74) *Attorney, Agent, or Firm* — Womble Bond Dickinson (US) LLP

(57) ABSTRACT

A membrane body for a tubular treatment device includes a tubular membrane portion (12). The membrane portion forms a multi-layer structure having a first layer (21) formed of a fiber and a second layer (22) having liquid permeability lower than that of the first layer.

3 Claims, 3 Drawing Sheets

MEMBRANE BODY FOR TUBULAR TREATMENT DEVICE AND TUBULAR TREATMENT DEVICE

BACKGROUND OF THE INVENTION

Field of the Invention

The present invention relates to a membrane body for a tubular treatment device and a tubular treatment device.

Description of the Related Art

For example, in the related art, a stent graft is known as a tubular treatment device used for treating an aortic aneurysm or an aortic dissection appearing in an aorta (for example, refer to Japanese Patent No. 6131441 and Japanese Patent No. 5824759).

For example, the stent graft includes a skeleton portion using a metal wire and a membrane portion covering the skeleton portion, and has a tubular outer shape as a whole. The stent graft expands by applying an external force from an inside to an outside in a radial direction at a predetermined position inside a blood vessel, and is caused to indwell the blood vessel in a state of being in close contact with the blood vessel.

It is preferable that a membrane portion of a stent graft has low liquid permeability in order to prevent blood from flowing into a lesion site when in use. On the other hand, when the membrane portion is fixed to a skeleton portion by suturing, depending on a material of the membrane portion, there is a possibility that the membrane portion may be torn or broken at a sutured location.

SUMMARY OF THE INVENTION

According to one aspect of the present invention, there is provided a membrane body for a tubular treatment device including a tubular membrane portion. The membrane portion forms a multi-layer structure having a first layer formed of a fiber and a second layer having liquid permeability lower than that of the first layer.

In addition, according to another aspect of the present invention, there is provided a tubular treatment device including a tubular membrane portion and a skeleton portion sutured to one surface of the membrane portion. The membrane portion forms a multi-layer structure having a first layer formed of a fiber and a second layer having liquid permeability lower than that of the first layer.

DESCRIPTION OF EMBODIMENTS

Figure 1:
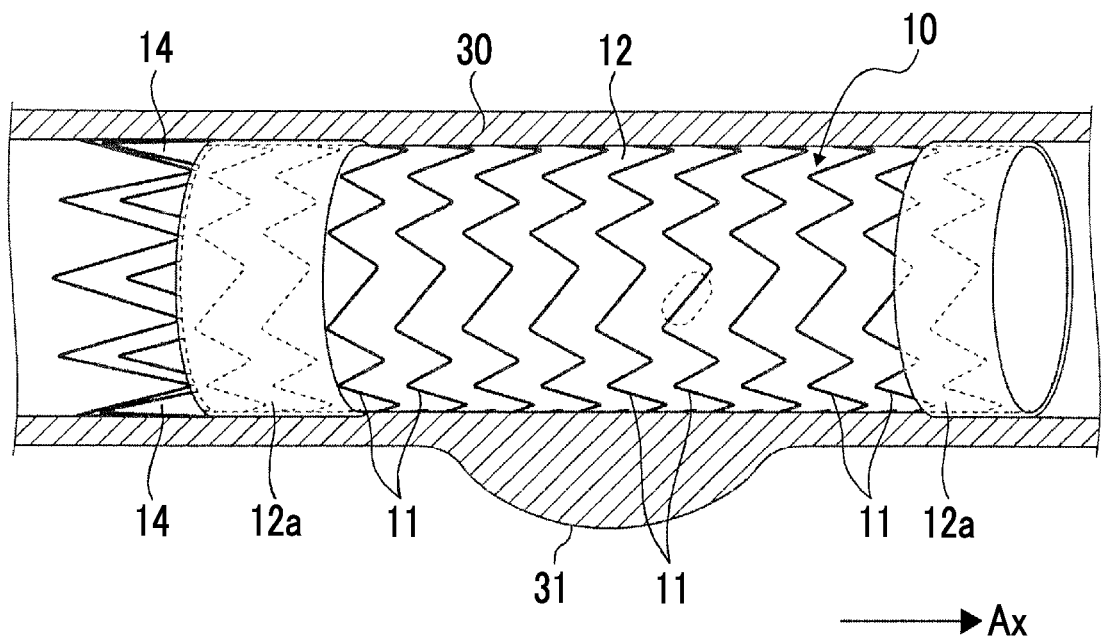
FIG. 1 is a perspective view of a stent graft according to an embodiment to which the present invention is applied.

Hereinafter, an embodiment of the present invention will be described with reference to the drawings.

Each drawing to be described later schematically illustrates a configuration example of a stent graft 10 serving as an embodiment of a tubular treatment device. A shape or a dimension of the stent graft 10 in the drawings is schematically illustrated, and does not indicate an actual shape or an actual dimension.

FIG. 1 is a perspective view illustrating a schematic configuration of the stent graft 10 according to the embodiment. FIG. 1 illustrates a state (used state) in which the stent graft 10 is caused to indwell a blood vessel.

The stent graft 10 illustrated in FIG. 1 is a stent graft for the blood vessel, and has a tubular shape as a whole. The stent graft 10 has openings provided in both end portions in an axial direction Ax and communicating with each other, and internally has a tubular flow path through which blood of a patient passes in the used state.

In an example in FIG. 1, the stent graft 10 having a straight tube shape is illustrated. However, for example, the stent graft 10 of the present embodiment may have a shape curved in an arch shape (for example, a shape corresponding to an aortic arch of the patient), or may have a twisted shape.

The stent graft 10 has a so-called self-expandable configuration in which a shape of an expanded state is memorized. The stent graft 10 is introduced into a blood vessel 30 in a state where the stent graft 10 is contracted inward in a radial direction (not illustrated) by being accommodated in a tubular sheath (not illustrated). The stent graft 10 is delivered to a predetermined position (for example, a lesion site 31 where an aortic aneurysm appears) inside the blood vessel 30. Thereafter, the stent graft 10 is released from the sheath, and expands outward in the radial direction. As illustrated in FIG. 1, the expanded stent graft 10 is caused to indwell the blood vessel 30 in a state of being in close contact with an inner wall of the blood vessel 30.

As illustrated in FIG. 1, the stent graft 10 includes a skeleton portion 11 and a membrane portion 12 fixed to the skeleton portion 11. The membrane portion 12 is an example of a membrane body for a tubular treatment device. In addition, for example, a bare portion 14 having a metal skeleton is formed in one end of the stent graft 10 in the axial direction Ax.

The bare portion 14 has a function of generating friction with the inner wall of the blood vessel 30 when the stent graft 10 is caused to indwell the blood vessel and preventing misalignment (migration) of the stent graft 10.

For example, the skeleton portion 11 is formed by spirally winding a thin metal wire (wire rod). For example, the skeleton portion 11 is formed by spirally winding the thin metal wire while bending the thin metal wire so that a peak portion and a valley portion are alternately formed. For example, a cross-sectional shape of the thin metal wire of the skeleton portion 11 is a circular shape or an elliptical shape.

The skeleton portion 11 is configured to be deformable so that the skeleton portion 11 is self-expandable from a contracted state of being contracted inward in the radial direction to an expanded state of being expanded outward in the radial direction.

For example, a material forming the thin metal wire of the skeleton portion 11 includes known metal or metal alloy represented by Ni—Ti alloy (Nitinol), cobalt-chromium alloy, titanium alloy, and stainless steel. The skeleton portion 11 may be formed of a material other than the metal (for example, ceramic or a resin).

In addition, for example, a material (nitinol or the like) of the skeleton portion 11, a cross-sectional area and a cross-sectional shape of the thin metal wire of the skeleton portion 11 (circular wire rod such as a wire, or square wire rod obtained by laser cutting), the number of folded times and a folded shape of the skeleton portion 11 in a circumferential direction (number of peak portions and a shape of peak portions), or a spiral pitch of the skeleton portion 11 in the axial direction (skeleton amount per unit length of the stent graft 10) can be set to a suitable value, depending on a diameter of an indwelling target blood vessel. Detailed description relating to the parameters will be omitted.

The membrane portion 12 is a tubular flexible membrane body that forms the above-described tubular flow path, and is attached to the skeleton portion 11 to close a gap portion of the skeleton portion 11. In the present embodiment, as illustrated in FIG. 1, the membrane portion 12 is attached to the inside of the skeleton portion 11. In addition, outer membrane portions 12a that partially cover the skeleton portion 11 from the outside are attached to both end portions of the stent graft 10 in the axial direction Ax.

For example, the outer membrane portion 12a may be formed by folding the membrane portion 12 from the inside to the outside of the skeleton portion 11. Alternatively, the outer membrane portion 12a may be formed by overlapping the membrane portion 12 formed in a band shape from the outside of the skeleton portion 11.

The outer membrane portion 12a may be attached to entirely cover the skeleton portion 11 from the outside, that is, to pinch and cover the skeleton portion 11 from the inside and the outside by using the two membrane portions 12.

In addition, the membrane portion 12 may be attached only to the outside of the skeleton portion 11.

Figure 3:
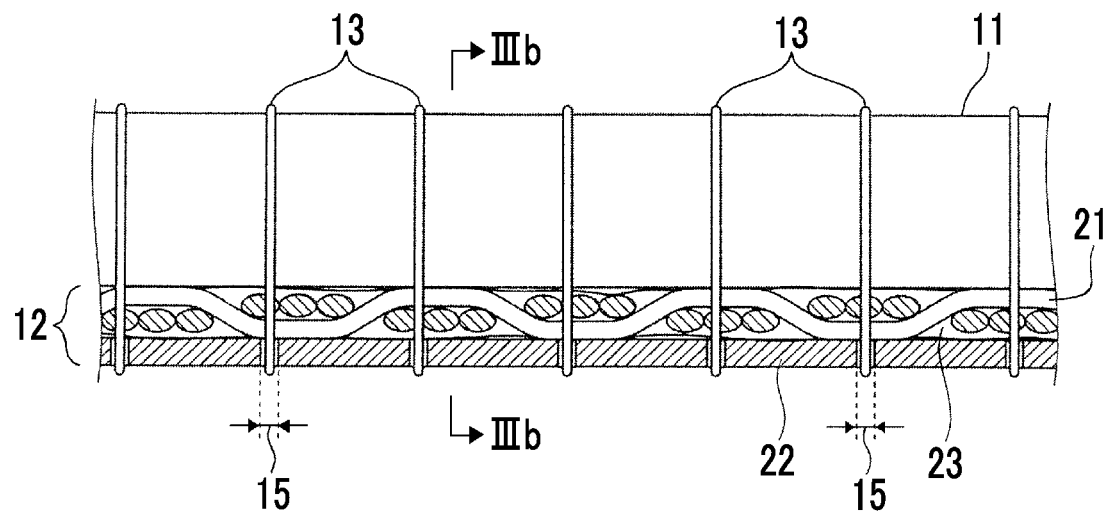
FIG. 3 is a view schematically illustrating a cross-sectional structure of a portion surrounded by a broken line in FIG. 1.
Figure 4:
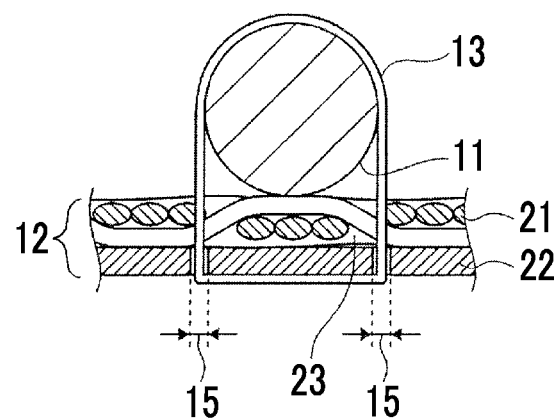
FIG. 4 is a sectional view taken along line IIIb-IIIb in FIG. 3.

As illustrated in FIGS. 3 and 4 (to be described later), the skeleton portion 11 of the present embodiment is sutured with the membrane portion 12 and a thread 13. For example, a method of fixing the skeleton portion 11 and the membrane portion 12 may be adhesion, welding, or sticking with a tape.

Figure 2:
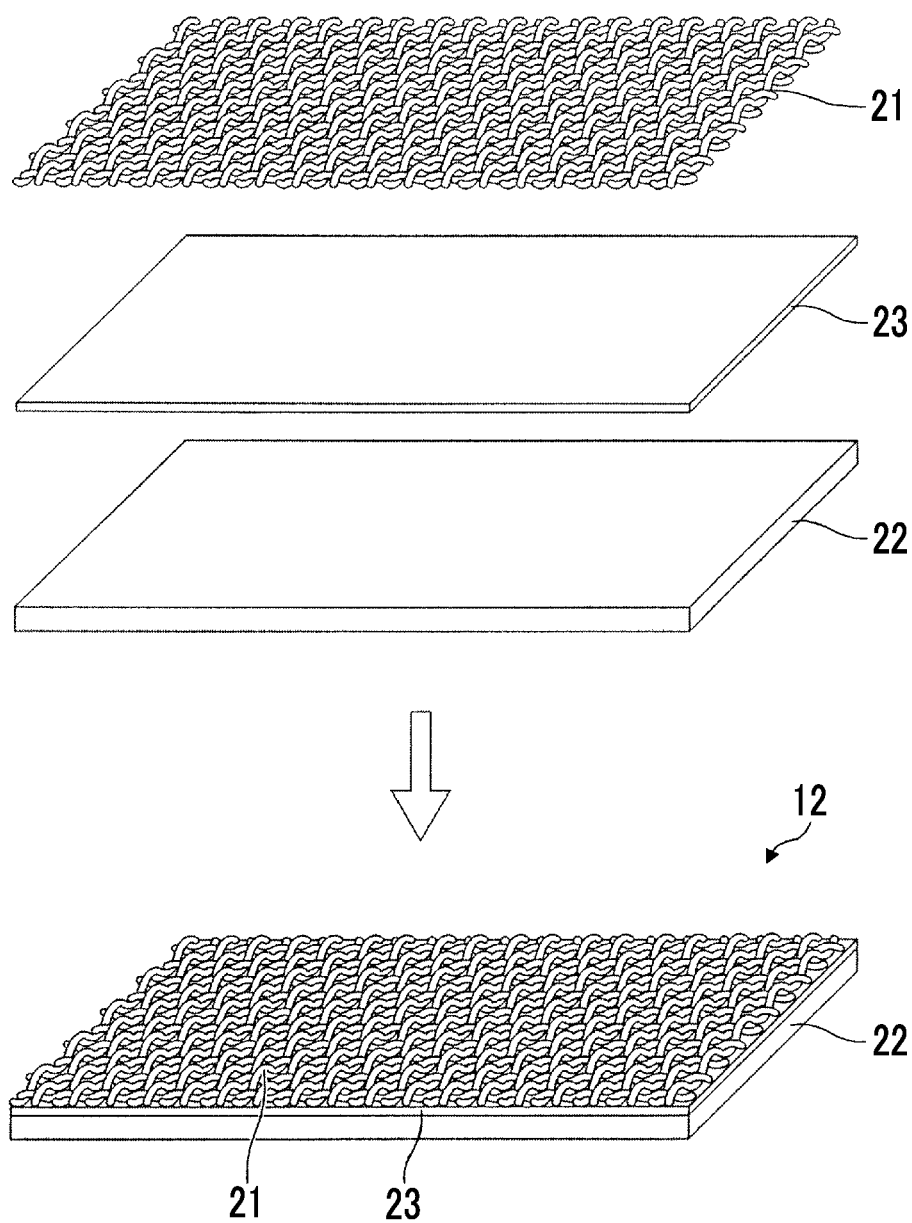
FIG. 2 is a view schematically illustrating a configuration of a membrane portion.

FIG. 2 is a view schematically illustrating a configuration of the membrane portion 12. In addition, FIG. 3 is a view schematically illustrating a cross-sectional structure of a portion surrounded by a broken line in FIG. 1. FIG. 4 is a sectional view taken along line IIIb-IIIb in FIG. 3.

The membrane portion 12 is a membrane body having a multi-layer structure in which a first layer 21 formed of a fiber and a second layer 22 having liquid permeability lower than that of the first layer 21 are stacked. In addition, an adhesive layer 23 for adhering the first layer 21 and the second layer 22 is formed as an intermediate layer between the first layer 21 and the second layer 22.

For example, the first layer 21 is a fabric in which fibers are disposed in a mesh pattern, and is configured to include a woven fabric, a knitted fabric, or a non-woven fabric of a biocompatible fiber material. The first layer 21 mainly has a function of preventing a portion sutured with the thread 13 from being torn or broken. For example, a fiber material of the first layer 21 includes a polyester resin such as polyethylene terephthalate and a fluororesin such as polytetrafluoroethylene (PTFE).

Although FIGS. 3 and 4 schematically illustrate an example in which the first layer 21 is formed of a woven fabric, the membrane portion 12 may be a knitted fabric or a non-woven fabric as described above. A weaving method of the woven fabric of the first layer 21 may be any of plain weaving, twill weaving, and satin weaving.

The second layer 22 is configured to include a non-liquid permeable film formed by stretching or rolling a biocompatible material. For example, a material of the second layer 22 includes a fluororesin such as polytetrafluoroethylene (PTFE). However, a polyester resin such as polyethylene terephthalate may be used.

The second layer 22 has a function of preventing a leakage of a body fluid between the inside and the outside of the stent graft 10. When the stent graft 10 is used, the blood flows into the stent graft 10. However, the second layer 22 has the non-liquid permeability. Accordingly, it is possible to prevent the blood inside the stent graft 10 from flowing into the lesion site 31 located outside the stent graft 10.

Although a fine hole is formed in a fiber gap in the fabric of the first layer 21, there are no fiber gap in the fabric on a surface of the second layer 22. Therefore, the second layer 22 has liquid permeability lower than that of the first layer 21.

The adhesive layer 23 may be any desired layer that can adhere the fabric of the first layer 21 and the second layer 22. When heating is performed during the adhering, a material having a melting point lower than that of the first layer 21 and the second layer 22 is used for the adhesive layer 23. For example, a material of the adhesive layer 23 includes silicone, urethane, or polyethylene.

As an example, silicone is adhered to at least an adhesive surface on the second layer 22 side of the fabric of the first layer 21 by dipping, and the fabric of the first layer 21 to which the silicone is adhered and a film of the second layer 22 are heated after both overlap each other. In this manner, the first layer 21 and the second layer 22 can be adhered to each other with the silicone.

The adhesive layer 23 in the membrane portion 12 is not essential, and the first layer 21 and the second layer 22 may be fixed to each other by a method other than the adhering. For example, any surface of the first layer 21 and the second layer 22 is subjected to a surface modification treatment, and affinity between the first layer 21 and the second layer 22 is increased to join both the layers to each other. In this manner, the adhesive layer 23 may be omitted.

In the present embodiment, the skeleton portion 11 is sutured to the membrane portion 12 having a multi-layer structure in which the fabric of the first layer 21 and the film of the second layer 22 are stacked. In this case, the thread 13 for suturing the skeleton portion 11 and the membrane portion 12 passes through a fiber gap in the first layer 21 of the membrane portion 12, and penetrates the second layer 22 of the membrane portion 12. Therefore, when the thread 13 passes through the second layer 22 during the suturing, an opening 15 as illustrated in FIGS. 3 and 4 is formed in the second layer 22.

Here, the stent graft 10 expands outward in the radial direction when in use. Accordingly, a force stretching in the circumferential direction acts on the membrane portion 12 of the stent graft 10 when in use.

In addition, when periodic vibrations generated by pulsations of the blood vessel are applied to the stent graft 10 when in use, the skeleton portion 11 and the membrane portion 12 may be affected by the vibrations, and may be misaligned on a peripheral surface of the stent graft 10. Due to the force that causes the misalignment, a force in a shearing direction acts between the thread 13 for suturing the skeleton portion 11 and the membrane portion 12 and the membrane portion 12.

When the above-described force acts on the membrane portion 12 in a complex manner, for example, a portion of the opening 15 of the second layer 22 where stress is likely to be concentrated is likely to be torn or broken. However, the membrane portion 12 has a multi-layer structure having the first layer 21 formed of a fiber and the second layer 22. Accordingly, the fibers disposed in a mesh pattern in the first layer 21 serve as resistance against a force for widening the opening 15 of the second layer 22. Therefore, strength around the opening 15 of the second layer 22 is reinforced by the first layer 21, and the sutured second layer 22 is less likely to be torn or broken.

In addition, with regard to a positional relationship between the membrane portion 12 and the skeleton portion 11, the membrane portion 12 may be attached so that the first layer 21 faces the skeleton portion 11, or the membrane portion 12 may be attached so that the second layer 22 faces the skeleton portion 11. For example, the membrane portion 12 is attached so that the second layer 22 is located inward. In this manner, the second layer 22 which is smoother than the first layer 21 and has high antithrombotic property can easily come into contact with the blood. In this manner, it is possible to adopt a configuration in which the stent graft 10 is less likely to be occluded by a thrombus. In particular, the configuration is useful for a small-diameter stent graft which is more likely to be occluded.

In the present embodiment, as illustrated in FIGS. 3 and 4, the membrane portion 12 is attached to the inside of the skeleton portion 11 so that the first layer 21 faces the skeleton portion 11.

As described above, the periodic vibrations generated by the pulsations of the blood vessel are applied to the stent graft 10, thereby causing a possibility that the skeleton portion 11 and the membrane portion 12 may be misaligned on the peripheral surface of the stent graft 10. However, when the first layer 21 faces the skeleton portion 11, the fabric of the first layer 21 comes into contact with the skeleton portion 11, and the skeleton portion 11 and the second layer 22 do not come into direct contact with each other. Therefore, when the above-described skeleton portion 11 and the membrane portion 12 are misaligned, it is possible to prevent the second layer 22 having a function of the non-liquid permeability from being worn by rubbing against the skeleton portion 11.

In addition, when the first layer 21 faces the outside of the stent graft 10, surface roughness of the first layer 21 is relatively large due to unevenness of the fiber. Accordingly, compared to a case where the membrane portion 12 is a smooth surface, a contact area between the skeleton portion 11 and the membrane portion 12 is reduced. Therefore, even when the skeleton portion 11 and the membrane portion 12 are misaligned due to the pulsations of the blood vessel, it is possible to adopt a configuration in which the membrane portion 12 is less likely to be worn.

On the other hand, although illustration is omitted, when the membrane portion 12 is attached to the inside of the skeleton portion 11 so that the second layer 22 faces the skeleton portion 11, the second layer 22 faces an outer peripheral side of the stent graft 10. In this case, when the stent graft 10 is used, the second layer 22 having the function of the non-liquid permeability is pressed against the inner wall of the blood vessel. Accordingly, the inner wall of the blood vessel and the second layer 22 are easily brought into close contact with each other. For example, a gap between the inner wall of the blood vessel and the second layer 22 is less likely to be formed in an end portion of the stent graft 10. Accordingly, the blood is more easily prevented from flowing into the lesion site 31 from the end portion of the stent graft 10.

As described above, the stent graft 10 of the present embodiment includes the tubular membrane portion 12 and the skeleton portion 11 sutured to one surface of the membrane portion 12. The membrane portion 12 is a membrane body having the multi-layer structure having the first layer 21 formed of the fiber and the second layer 22 having liquid permeability lower than that of the first layer 21.

According to the present embodiment, the membrane portion 12 has the second layer 22 having low liquid permeability. Accordingly, a leakage of a body fluid between the inside and the outside of the stent graft 10 is can be prevented, and the blood inside the stent graft 10 can be prevented from flowing into the lesion site 31 located outside the stent graft 10.

In addition, the membrane portion 12 has a multi-layer structure having the first layer 21 formed of the fiber and the second layer 22. Accordingly, the fibers disposed in a mesh pattern in the first layer 21 serve as resistance against a force for widening the opening 15 of the second layer 22 which is formed by the thread 13 passing therethrough. Therefore, according to the present embodiment, the sutured second layer 22 is less likely to be torn or broken.

In addition, according to the stent graft 10 including the membrane portion 12 having the multi-layer structure of the present embodiment, a thickness of the whole membrane portion 12 can be reduced, compared to a case where the membrane portion is configured to include only the fabric or only a film-like membrane body.

As an example, when the membrane portion is configured to include only the fabric, the membrane portion needs to be thickened to degrade liquid permeability.

In addition, when the membrane portion is configured to include only the film-like membrane body, it is relatively easy to ensure non-liquid permeability. However, for example, when sutured to the skeleton portion, there is a possibility that the body fluid may leak due to a torn or broken portion from a sutured location. Therefore, even when the membrane portion is configured to include only the film-like membrane body, the thickness of the membrane portion needs to be thickened to prevent the membrane portion from being torn or broken.

When the membrane portion is thickened as described above, there is a possibility of poor storability when the tubular treatment device is stored in the sheath and degraded release property from the sheath.

In contrast, according to the present embodiment, the membrane portion 12 has the multi-layer structure. The first layer 21 is responsible for ensuring the strength against tearing or breaking, and the second layer 22 is responsible for ensuring the non-liquid permeability. Therefore, it is not necessary to respectively thicken the first layer 21 and the second layer 22. As a result, the overall thickness of the membrane portion 12 can be reduced. In this manner, according to the present embodiment, it is possible to adopt a technique for stent graft indwelling using a sheath having a smaller diameter than that in the related art, and it is possible to further reduce a load (invasiveness) of a patient during surgery.

In addition, according to the present embodiment, the membrane portion 12 is attached to the inside of the skeleton portion 11 so that the first layer 21 faces the skeleton portion 11 (FIGS. 3 and 4). Therefore, the skeleton portion 11 comes into contact with the fabric of the first layer 21, but does not come into contact with the second layer 22. Accordingly, it is possible to prevent the second layer 22 from being worn by rubbing against the skeleton portion 11.

Furthermore, according to the present embodiment, the outer membrane portions 12a that partially cover the skeleton portion 11 from the outside are formed in both ends of the stent graft 10 in the axial direction Ax (FIG. 1). Here, the outer membrane portion 12a of the stent graft 10 is disposed so that the second layer 22 faces the outer peripheral side of the stent graft 10. In this manner, the inner wall of the blood vessel and the second layer 22 are in close contact with each other. Accordingly, a gap is less likely to be formed between the inner wall of the blood vessel and the second layer 22. In this manner, the blood is more easily prevented from flowing into the lesion site 31 from the end portion of the stent graft 10.

As described above, the present invention is not limited to the above-described embodiment, and various improvements and design changes may be made within the scope not departing from the concept of the present invention.

For example, in the above-described embodiment, a configuration has been described in which the first layer 21 and the second layer 22 are provided one by one as the membrane portion 12. However, the membrane portion 12 may have either a plurality of the first layers 21 or a plurality of the second layers 22. For example, the membrane portion 12 may be a membrane body having the multi-layer structure in which the second layer 22 is disposed between two first layers 21, or may be a membrane body having the multi-layer structure in which the first layer 21 is disposed between two second layers 22.

In addition, in the membrane portion 12, the first layer 21 which is responsible for ensuring the strength against tearing or breaking may not be disposed in the whole membrane portion 12. For example, the first layer 21 may be partially provided to be aligned with the position of the skeleton portion 11 on the peripheral surface of the membrane portion 12, and the sutured location of the skeleton portion 11 may be partially reinforced.

In addition, for example, the first layer 21 may contain a polymer compound such as polyethylene (particularly, an ultrahigh molecular weight polyethylene having a molecular weight of approximately 1 million to 6 million). In this manner, the first layer 21 can be provided with sliding property, and resistance can be reduced when the stent graft 10 is loaded into the sheath or when the stent graft 10 is released from the sheath. In addition, the liquid permeability of the first layer 21 may be lowered by filling the fiber gap of the first layer 21 with the polymer compound and closing the gap.

In addition, the embodiment described herein is merely an example in all respects, and should be considered that the embodiment is not limited. The scope of the present invention is represented by the appended claims without being limited to the above description, and the present invention intends to include all modifications within the meaning and the scope which are equivalent to those of the appended claims.

What is claimed is:

1. A stent graft comprising:
   a tubular membrane portion; and
   a self-expandable skeleton portion formed by a metal wire wound around an axial center of the stent graft, the skeleton portion sutured to one surface of the membrane portion with thread,
   wherein the membrane portion forms a multi-layer structure having a first layer made of a woven polyester resin fiber; a second layer having liquid permeability lower than that of the first layer and made of a membrane body formed of polytetrafluoroethylene (PTFE); and an intermediate adhesive layer adhering the first layer and the second layer, wherein the adhesive layer comprises silicone,
   the first layer has a fiber gap formed by mutually orthogonal fibers of the woven, the fiber gap is filled with silicone,
   the thread for suturing the skeleton portion to the membrane portion passes through the fiber gap in the first layer of the membrane portion and penetrates the second layer,
   the membrane portion provides resistance to a force for widening an opening of the second layer caused by suturing, using the fibers of the woven in which the fiber gap is filled with the silicone.

2. The stent graft according to claim 1, wherein the woven is any one of plain weave, twill weave, and satin weave.

3. The stent graft according to claim 1, wherein the membrane portion is attached so that the first layer faces the skeleton portion.

* * * * *